United States Patent
Kim et al.

(10) Patent No.: US 8,721,547 B2
(45) Date of Patent: May 13, 2014

(54) ULTRASOUND SYSTEM AND METHOD OF FORMING ULTRASOUND IMAGE

(71) Applicant: Medison Co., Ltd., Kangwon-do (KR)

(72) Inventors: Sung Yun Kim, Seoul (KR); Jong Sik Kim, Seoul (KR)

(73) Assignee: Samsung Medison Co., Ltd., Gangwon-Do (KR)

( * ) Notice: Subject to any disclaimer, the term of this patent is extended or adjusted under 35 U.S.C. 154(b) by 0 days.

(21) Appl. No.: 13/692,811

(22) Filed: Dec. 3, 2012

(65) Prior Publication Data

US 2013/0123633 A1  May 16, 2013

Related U.S. Application Data

(63) Continuation of application No. 12/044,292, filed on Mar. 7, 2008.

(30) Foreign Application Priority Data

Mar. 8, 2007 (KR) .................. 10-2007-0022982

(51) Int. Cl.
 *A61B 8/00* (2006.01)
(52) U.S. Cl.
 USPC .......................................... 600/449; 600/443
(58) Field of Classification Search
 USPC ......... 600/407, 433, 437, 438, 440, 443, 447, 600/454, 456, 459; 73/584
 See application file for complete search history.

(56) References Cited

U.S. PATENT DOCUMENTS

| | | | |
|---|---|---|---|
| 5,515,856 A * | 5/1996 | Olstad et al. | 600/440 |
| 5,570,430 A * | 10/1996 | Sheehan et al. | 382/128 |
| 6,002,738 A | 12/1999 | Cabral et al. | |
| 6,196,715 B1 | 3/2001 | Nambu et al. | |
| 6,464,642 B1 * | 10/2002 | Kawagishi | 600/454 |
| 8,103,066 B2 | 1/2012 | Kim et al. | |

(Continued)

FOREIGN PATENT DOCUMENTS

| | | |
|---|---|---|
| EP | 1 757 955 A1 | 2/2007 |
| JP | 2001-046372 A | 2/2001 |

(Continued)

OTHER PUBLICATIONS

Japanese Office Action with English Translation issued in Japanese Application No. 2008-058386 Feb. 19, 2013.

(Continued)

*Primary Examiner* — Parikha Mehta
*Assistant Examiner* — Michael N Fisher
(74) *Attorney, Agent, or Firm* — McDermott Will & Emery LLP

(57) ABSTRACT

The present invention is directed to an ultrasound system capable of providing a plurality of M-mode images corresponding to M-mode lines without moving a probe. A volume data forming and reconstructing unit of the present invention forms volume data based on the ultrasound echo signals, the volume data forming and reconstructing unit being configured to determine a beat period of the moving object and reconstruct the volume data based on the beat period. A processor forms at least one reference image based on the reconstructed volume data and one or more M-mode images corresponding to one or more M-mode lines set on the reference image and a display unit displays the reference image, the M-mode lines and the M-mode images.

8 Claims, 8 Drawing Sheets

(56) References Cited

U.S. PATENT DOCUMENTS

| | | |
|---|---|---|
| 2002/0045826 A1 | 4/2002 | Powers et al. |
| 2004/0111028 A1 | 6/2004 | Abe et al. |
| 2004/0127798 A1 | 7/2004 | Dala-Krishna et al. |
| 2005/0049503 A1 | 3/2005 | Schoisswohl et al. |
| 2005/0245822 A1 | 11/2005 | Dala-Krishna et al. |
| 2005/0288589 A1 | 12/2005 | Houle et al. |
| 2007/0167809 A1 | 7/2007 | Dala-Krishna |
| 2008/0221450 A1 | 9/2008 | Kim et al. |

FOREIGN PATENT DOCUMENTS

| | | |
|---|---|---|
| JP | 2004-195253 A | 7/2004 |
| JP | 2005-040598 A | 2/2005 |
| JP | 2005-074225 A | 3/2005 |
| KR | 2002-44563 | 6/2002 |
| KR | 2008-0001059 A | 1/2008 |
| KR | 2008-0029189 A | 4/2008 |
| WO | WO-02/17298 | 2/2002 |

OTHER PUBLICATIONS

Japanese Notice of Allowance with English Translation issued in Japanese Applicaiton No. 10-2007-0022982 mailed Apr. 26, 2013.
European Office Action issued in European Patent Application No. 08004218.7 dated Oct. 5, 2012.
Extended European Search Report issued Jan. 25, 2012, in Patent Application No. 08004218.7.
Japanese Office Action issued in Japanese Patent Application No. JP 2008-058386 dated Jan. 20, 2014.

* cited by examiner

ULTRASOUND SYSTEM AND METHOD OF FORMING ULTRASOUND IMAGE

The present application is a Continuation Application of U.S. application Ser. No. 12/044,292, filed Mar. 7, 2008, which claims priority from Korean Patent Application No. 10-2007-0022982 filed on Mar. 8, 2007, the entire subject matter of which is incorporated herein by reference.

BACKGROUND OF THE INVENTION

1. Technical Field

The present invention generally relates to ultrasound systems, and more particularly to an ultrasound system and a method of forming ultrasound images.

2. Background Art

An ultrasound system has become an important and popular diagnostic tool due to its non-invasive and non-destructive nature. Modern high-performance ultrasound imaging diagnostic systems and techniques are commonly used to produce two- or three-dimensional images of internal features of patients.

The ultrasound system generally uses a probe comprising an array of transducer elements to transmit and receive ultrasound signals. The ultrasound system forms an image of human internal tissues by electrically exciting transducer elements to generate ultrasound signals that travel into the body. Echoes reflected from tissues and organs return to the transducer elements and are converted into electrical signals, which are amplified and processed to produce an ultrasound image data.

The ultrasound system provides an M-mode (motion mode) image periodically showing the motion of a target object. The ultrasound system first displays a B-mode image of the target object and then displays bio-information of the target object, which corresponds to an M-mode line set on the B-mode image, over the elapse of time.

In the conventional ultrasound system, however, a probe should be moved to observe different portions of a target object. Thus, there are problems in that B-mode and M-mode images for different portions of the target object cannot be provided at the same time. Further, it takes a long time to form the B-mode and M-mode images for different portions of the target object.

DETAILED DESCRIPTION OF THE INVENTION

Figure 1:
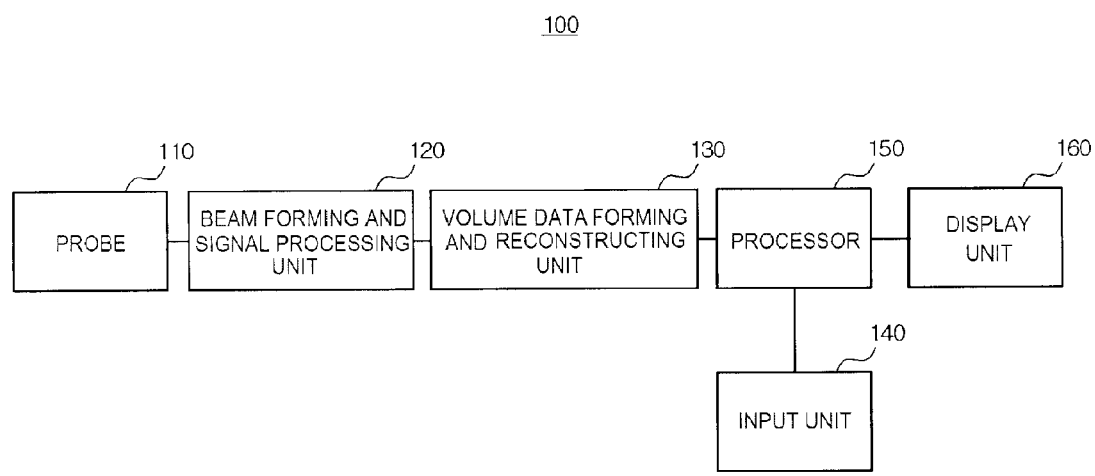
FIG. 1 is a block diagram showing an ultrasound system in accordance with one embodiment of the present invention.

FIG. 1 is a block diagram showing an ultrasound system constructed in accordance with the present invention. As shown in FIG. 1, the ultrasound system 100 includes a probe 110, a beam forming and signal processing unit 120, a volume data forming and reconstructing unit 130, an input unit 140, a processor 150 and a display unit 160. The ultrasound system 100 may further include a storage unit (not shown) for storing various data.

The probe 110 may include an array transducer containing a plurality of transducer elements for transmitting ultrasound signals to a target object and receiving ultrasound echo signals from the target object. The target object may contain a periodically moving object. The transducer elements may convert the ultrasound echo signals into electrical reception signals.

The beam forming and signal processing unit 120 may be operable to focus the electrical reception signals, and amplify and process the focused signals. The volume data forming and reconstructing unit 130 may form volume data for a 3-dimensional ultrasound image of the target object based on the focused signals received from the beam forming and signal processing unit 120. The volume data forming and reconstructing unit 130 may be operable to calculate a beat period of the moving object contained in the target object and reconstruct the volume data based on the calculated beat period. When the object is a heart, the beat period may be a heartbeat period.

Figure 2:
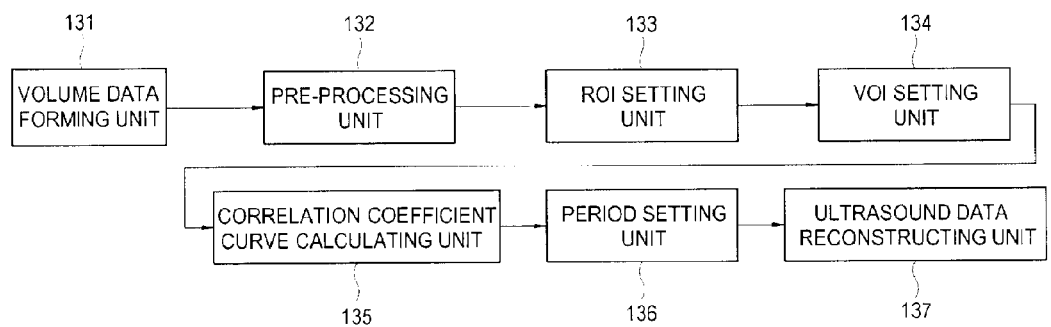
FIG. 2 is a block diagram showing a volume data forming and reconstructing unit in accordance with one embodiment of the present invention.

As shown in FIG. 2, the volume data forming and reconstructing unit 130 may include a volume data forming unit 131, a pre-processing unit 132, a region of interest (ROI) setting unit 133, a volume of interest (VOI) setting unit 134, a correlation coefficient calculating unit 135, a period setting unit 136 and a volume data reconstructing unit 137.

The volume data forming unit 131 may form volume data for forming a 3-dimensional ultrasound image of the target object based on the focused signals, which are consecutively received from the beam forming and signal processing unit 120.

Figure 3:
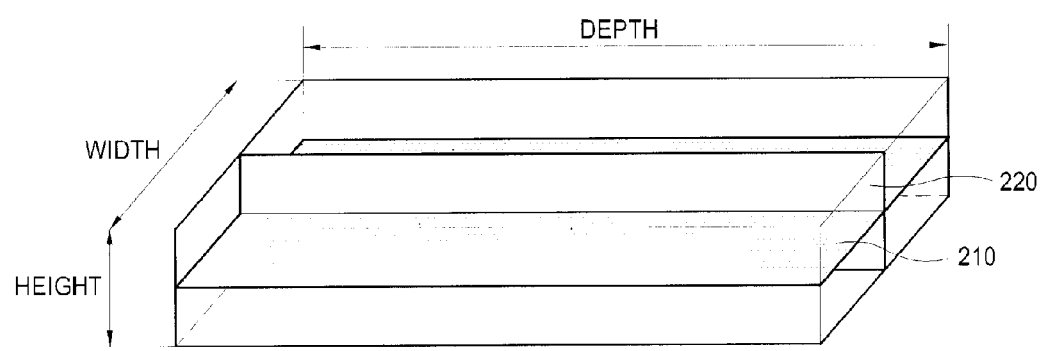
FIG. 3 is a schematic diagram showing cut plane images in volume data.

The pre-processing unit 132 may be operable to reduce or remove noises from an ultrasound image. The noise reduction may preferably be performed upon at least one of horizontal and vertical cut plane images 210 and 220, which are obtained by horizontally or vertically cutting the ultrasound volume data, as shown in FIG. 3. Generally, since data corresponding to an object desired for observation are positioned at a center portion of the volume data, the volume data may be cut either in the horizontal or vertical direction along its center planes. As discussed below, the noise reduction is assumed to be performed upon the horizontal cut plane image 210.

The pre-processing unit 132 may decompose the horizontal cut plane image in a wavelet domain into sub-band images HH, HL, LH and LL (wavelet transform). The pre-processing unit 132 may calculate wavelet coefficients in each sub-band image. The pre-processing unit 132 may perform soft-thresholding upon the calculated wavelet coefficients. That is, if the calculated wavelet coefficient is smaller than the threshold, then the pre-processing unit 132 may reset the wavelet coefficient to zero. If the wavelet coefficient is greater than the threshold, then the pre-processing unit 132 may subtract the threshold from the wavelet coefficient to thereby reset the wavelet coefficient. The soft-thresholding may not be carried out for the sub-band image LL, wherein the sub-band image LL represents low frequency (vertical)—low frequency (horizontal) image. The soft-thresholding can be carried out by the following equation in accordance with the present invention.

$$W_j\hat{f}(t) = \text{sign}(W_jf(t))[|W_jf(t)| - Th]_+, \ [x]_+ = \begin{cases} x, & x > 0 \\ 0, & \text{otherwise} \end{cases} \quad (1)$$

wherein, $W_jf(t)$ represents a coefficient of a high frequency at a $j^{th}$ level decomposed in the wavelet domain, sign() represents a sign of the coefficients, Th represents a threshold having a constant value, and $W_j\hat{f}(t)$ represents a resulting wavelet coefficient from performing the soft-thresholding. Thereafter, the pre-processing unit 132 may reconstruct the decomposed images through inverse wavelet transform to thereby obtain the horizontal cut plane image with the noises reduced.

Figure 4:
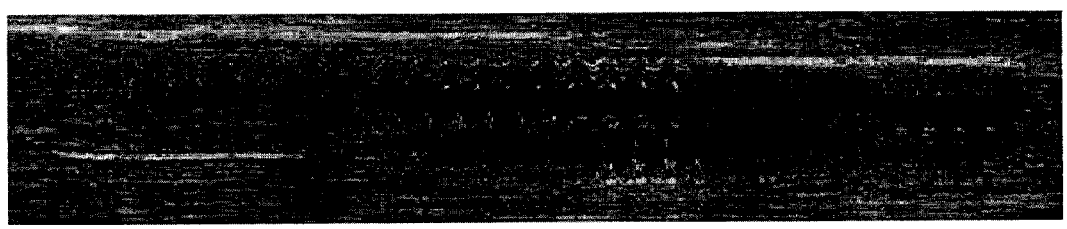
FIG. 4 is a photo showing a horizontal cut plane image in volume data.
Figure 5:
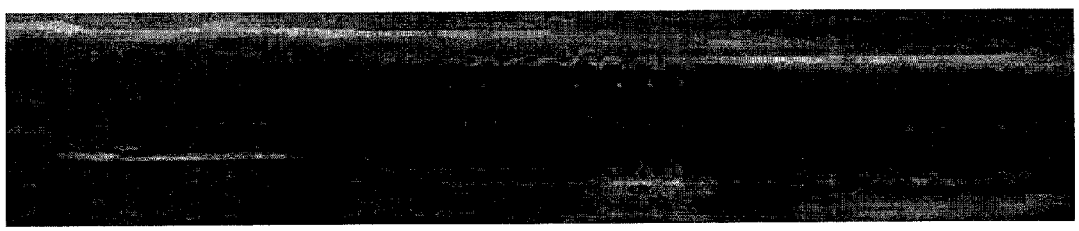
FIG. 5 is a photo showing an image obtained by performing soft-thresholding upon a horizontal cut plane image.

FIG. 4 shows an original horizontal cut plane image obtained from the ultrasound volume data, whereas FIG. 5 shows a horizontal cut plane image obtained by reconstructing the sub-band images with the soft-thresholding performed in the pre-processing unit 132.

Figure 6:
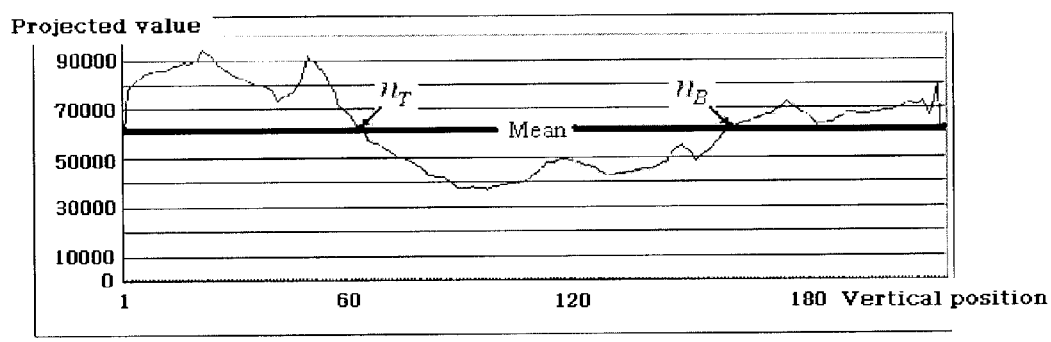
FIG. 6 is a graph showing projected values obtained through the horizontal projection of a horizontal cut plane image.

The ROI setting unit 133 may set a region of interest (ROI) on the pre-processed horizontal cut plane image. In order to set the ROI, the ROI setting unit 133 may perform horizontal projection upon the pre-processed horizontal cut plane image to thereby obtain projected values that are sum of the brightness of all pixels along horizontal projection lines, as shown in FIG. 6. The ROI setting unit 133 may calculate a mean value of the projected values and calculate positions $n_T$ and $n_B$, which represent a vertical position of a projected value located in the most left side among the projected values smaller than the mean value and a vertical position of a projected value located in the most-right side among the projected values smaller than the mean value, respectively. Positions $n_T$ and $n_B$ may be calculated by using equation (2) shown below.

$$n_T = \min_n\{n \mid f_n < \text{Mean}\}, \ 0 \le n < \frac{N}{2} \quad (2)$$

$$n_B = \max_n\{n \mid f_n < \text{Mean}\}, \ \frac{N}{2} \le n < N$$

wherein, $f_n$ represents a horizontally projected signal, and Mean represent a mean of the projected values. The positions $n_T$ and $n_B$ may be used as boundaries of the ROI.

Figure 7:
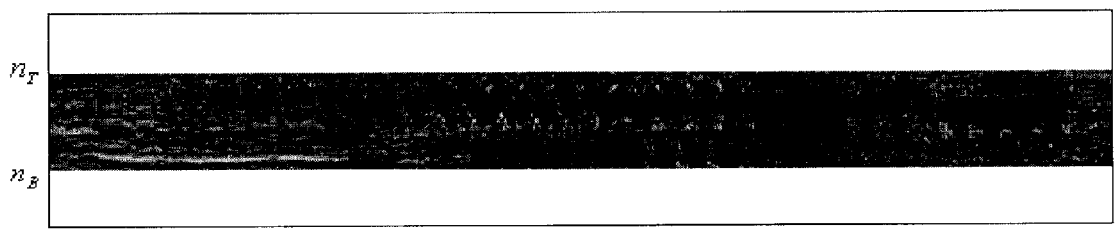
FIG. 7 is a photo showing an image with a horizontal cut plane image masked by a mask defining ROI boundaries.
Figure 8:
FIG. 8 is a photo showing the ROI set in a frame.

The ROI setting unit 133 may use the boundaries $n_T$ and $n_B$ of ROI to mask the horizontal cut plane image, thereby removing regions that are located outside the boundaries $n_T$ and $n_B$, as shown in FIG. 7. An example of the ROI set on an arbitrary frame in the ultrasound volume data is shown in FIG. 8.

The VOI setting unit 134 may be operable to set a volume of interest (VOI) in the volume data by using the ROI. The VOI setting unit 134 may select frames including the moving object within the target object. A plurality of vertical lines may be set in the horizontal cut plane image and standard deviation of brightness of the vertical lines may be used to select the frames. For example, the moving object may be the heart of a fetus. Since the heart includes valves (displayed in a bright portion) as well as atria and ventricles (displayed in a dark portion), the image of the heart relatively has a high contrast. Thus, the vertical lines including a heart region may be found by using the standard deviation of the brightness of the vertical lines. Also, since the contrast of neighboring vertical lines within the heart region rapidly changes, the vertical lines included in the heart region may be more accurately selected by considering standard deviation of the neighboring vertical lines. This is to allow the vertical lines, which are not included in the heart region and have a high contrast, to be excluded from the vertical lines included in the heart region.

The VOI setting unit 134 may select three vertical lines having a maximum standard deviation difference between the neighboring vertical lines in order to detect reference frames for setting VOIs. Pseudo codes of algorithm for selecting three vertical lines are as follows:

DO i=0,1,2
Step 1.

$$\hat{k}_i = \underset{k_i}{\arg\max}(|\sigma_{k_i} - \sigma_{k_{i-1}}|), \ (0 \le k_i < K)$$

Step 2. reject the range of $[k_i-C, K_i+C]$ in the search range
END DO wherein, $\sigma_{k_i}$ represents the standard deviation of the vertical lines existing on the horizontal cut plane image, $k_i$ represents an order of the vertical lines (identical to that of the frames in the volume), K represents the number of total frames (identical to that of total vertical lines), and C is a constant. Three frames including the three vertical lines obtained by the above algorithm are used as the reference frames for setting three VOIs.

Figure 9:
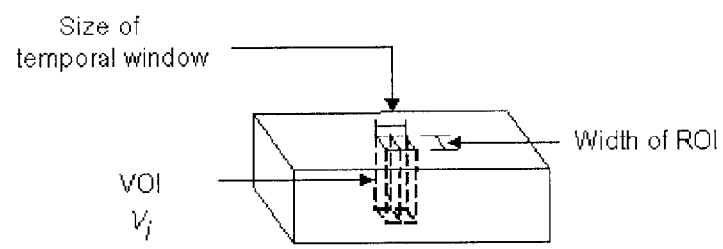
FIG. 9 is a schematic diagram showing an example of the VOI set in ultrasound volume data.

The VOI setting unit 134 may be operable to collect the neighboring frames of each of the three reference frames and set the VOIs with the ROIs set on the collected frames. FIG. 9 shows an example of the VOI set in the volume data. In FIG. 9, the length of the VOI on a time axis may be determined according to frames positioned at the right and left sides of the reference frame. The width of the VOI is defined according to the width of the ROI set in the ROI setting unit 133. The VOI set in the VOI setting unit 134 can be expressed as the following equation.

$$V_{\hat{k}_i} = \{f_{ROI}(k), \hat{k}_i - 1 \le k \le \hat{k}_i + 1\} \text{ for each } \hat{k}_i \quad (3)$$

wherein, $\hat{k}_i$ represents the positions of three vertical lines having a maximum standard deviation in the horizontal cut plane image (i.e., frame positions), $f_{ROI}(k)$ represents the ROI in a $k^{th}$ frame, and $V_{\hat{k}_i}$ represents the VOI formed by combining the ROI within the reference frame with those of neighboring frames. The VOI setting unit 134 may set three VOIs for three reference frames.

Figure 10:
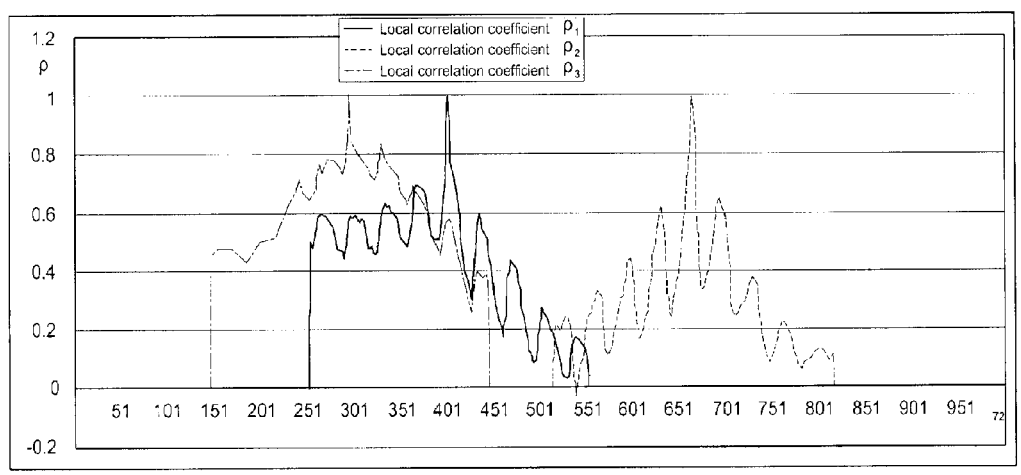
FIG. 10 is a graph showing three correlation coefficient curves.

The correlation coefficient curve calculating unit 135 may calculate the correlation coefficient curves for a constant time by using the VOIs set in the VOI setting unit 134. The correlation coefficient curve is calculated through the following equation.

$$\rho_i(V_k, V_{\hat{k}_i}) = \frac{E[V_k V_{\hat{k}_i}] - E[V_k]E[V_{\hat{k}_i}]}{\sigma_{V_k}\sigma_{V_{\hat{k}_i}}}, \quad (4)$$

$$(\hat{k}_i - 200 \leq k < \hat{k}_i + 200) \text{ for each } \hat{k}_i$$

wherein, $E[V_k]$ and $E[V_{\hat{k}_i}]$ represent the average of brightness within VOIs at k and $\hat{k}_i$ positions, $\sigma_{V_k}$ and $$\sigma_{V_{\hat{k}_i}}$$

represent the mean of standard deviation of brightness within the VOIs at k and $\hat{k}_i$ positions, and $\rho_i(V_k, V_{\hat{k}_i})$ represents a correlation coefficient between the VOI at a k position and the VOI at a $\hat{k}_i$ position. The correlation coefficient curve calculating unit 135 may calculate the three correlation coefficient curves for three VOIs, which are set in the VOI setting unit 134. The reason for calculating the three correlation curves is to utilize the local characteristics in volume data. FIG. 10 is a graph showing the three correlation coefficient curves obtained in the correlation coefficient curve calculating unit 135.

Figure 11:
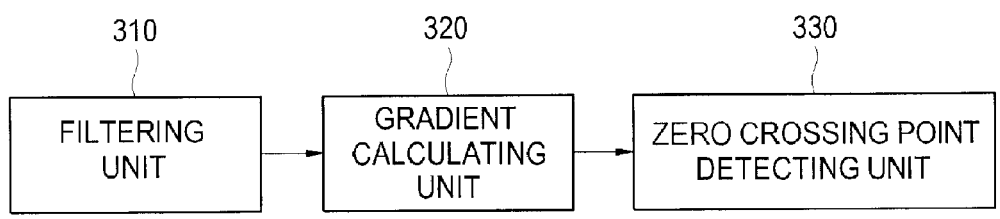
FIG. 11 is a block diagram showing a procedure of detecting a global period of heartbeat.

The period setting unit 136 may detect a heartbeat period. FIG. 11 is a block diagram showing a procedure for detecting the global period in the period setting unit 136. The period setting unit 136 may include a filtering unit 310, a gradient calculating unit 320 and a zero cross point detecting unit 330. The filtering unit 310 may be operable to filter the correlation coefficient curves to reduce noises included therein. A low pass filter may be used in the filtering unit 310. The gradient calculating unit 320 may calculate the gradients in the filtered correlation coefficient curves. The zero cross point detecting unit 330 may detect zero cross points whose gradients are changed from positive to negative.

Figure 12:
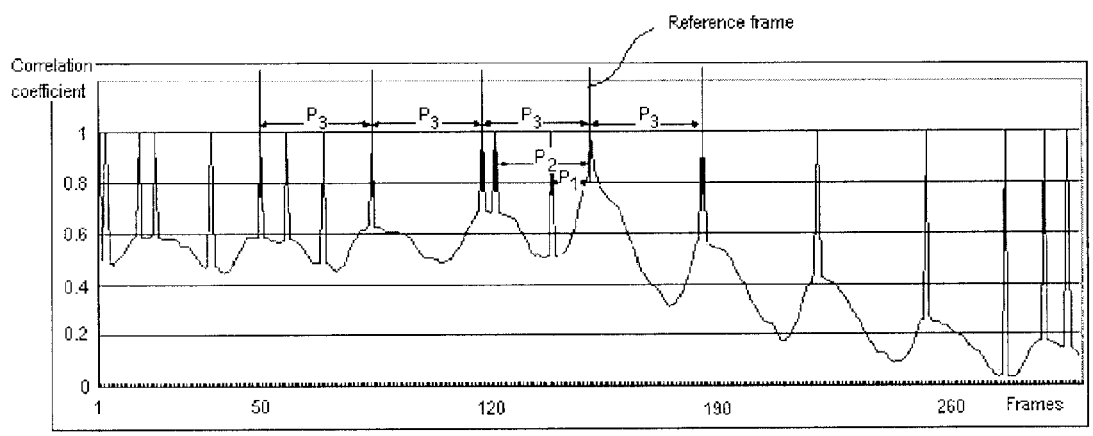
FIG. 12 is a diagram showing an example of detecting a global period of heartbeat.

Subsequently, the period setting unit 136 may set candidate periods by using right and left zero crossing points of a central zero crossing point at each of the three filtered correlation coefficient curves. That is, the period setting unit 136 may calculate six candidate periods of the heartbeat (Pn). FIG. 12 shows an example of detecting the heartbeat period in the filtered correlation coefficient curve. The period setting unit 136 may select one period ($P_3$) having the highest frequency among the candidate periods ($P_1$, $P_2$, $P_3$) and then set the selected period to a global period of the heartbeat. The period selection can be expressed as the following equation.

$$P_{FHB} = \text{mode}(p_n) \quad (5)$$

wherein, $P_n$ represents six candidate periods detected from three correlation coefficient curves formed from the VOI, and $P_{FHB}$ represents a period having the highest frequency among the six candidate periods.

Subsequently, the period setting unit 136 may set a new reference frame, which is away from the reference frame by the global period, and then set a search region including a predetermined number of frames adjacent to the new reference frame. The period setting unit 136 may be operable to calculate the correlation coefficients between the VOI in the reference frame and each VOI in each frame included in the search region. If a correlation coefficient of an arbitrary frame is maximal among the correlation coefficients of the frames included in the search region and the correlation of the arbitrary frame is greater than a value obtained by multiplying a predetermined weight by an average of the correlation coefficients, then an interval between the arbitrary frame and the reference frame is determined as the local period. Thereafter, the period setting unit 136 may set a new reference frame, which is away from the arbitrary frame by the global period. Then, the above process for calculating the local period is repeatedly carried out to the end of the volume data, thereby obtaining total local periods.

The ultrasound data reconstructing unit 137 may perform a linear interpolation for the frames included within each local period by using the global period set in the period setting unit 136. The ultrasound data reconstructing unit 137 may be operable to calculate a ratio (r) of the local period to the global period as the following equation.

$$r = \frac{\text{Local Period}}{\text{Global Period}} \quad (6)$$

Thereafter, an interpolation frame (I') is calculated as the following equation using the ratio (r) of the local period to the global period.

$$I' = \Delta_2 \times I_n + \Delta_1 \times I_{n+1} \quad (7)$$

wherein, $I_n$ and $I_{n+1}$ and represent frames adjacent to the interpolation frame I', $\Delta_1$ and $\Delta_2$ represent the distances between the adjacent frames and the interpolation frames, and wherein $\Delta_1$ and $\Delta_2$ are determined according to the ratio (r) of the local period to the global period. This interpolation process is carried out for frames included in all local periods such that the same number of frames is contained in each local period.

Figure 13:
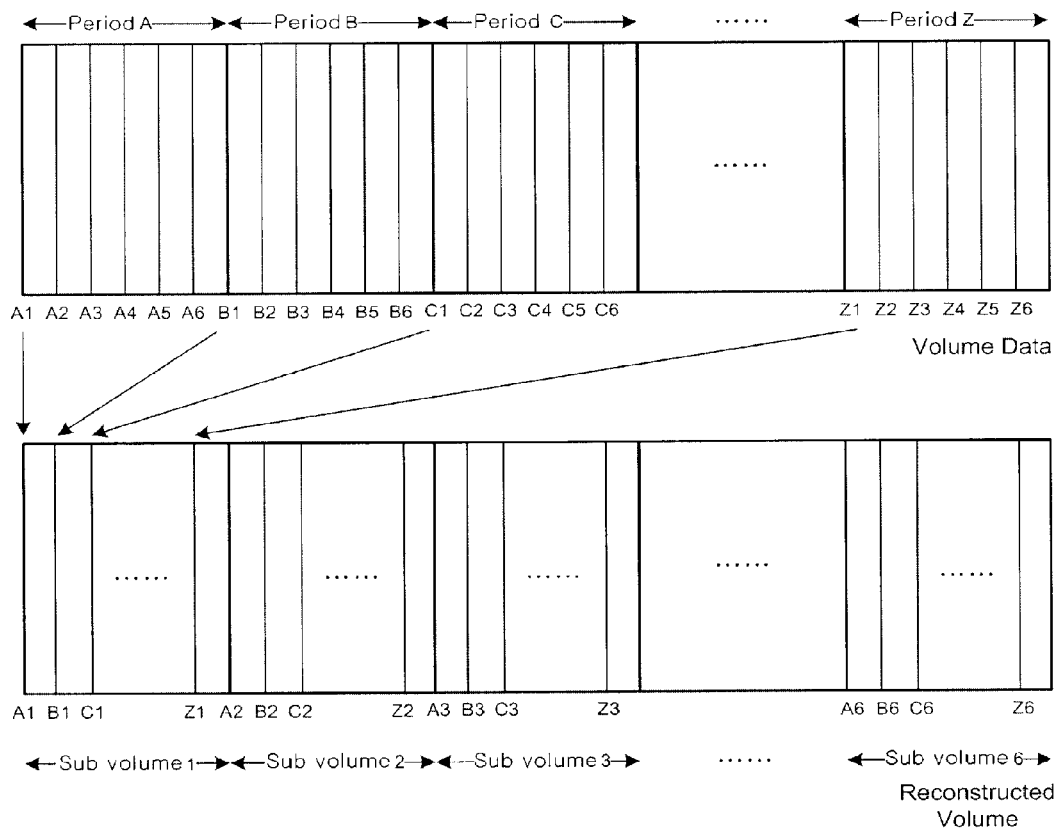
FIG. 13 is a diagram showing a procedure of reconstructing ultrasound volume data in accordance with one embodiment of the present invention.

The ultrasound data reconstructing unit 137 may reconstruct the interpolated volume data to provide a 3-dimensional ultrasound image showing a figure of the heartbeat. FIG. 13 shows a procedure for reconstructing the interpolated volume data. As shown in FIG. 13, twenty-six local periods A to Z may exist in one volume data. Assuming that six frames are contained in one local period in the volume data as shown in FIG. 13, the reconstructed volume data includes six sub volumes. Each of the sub volumes consists of 26 frames $A_i$ to $Z_i$.

Further, when the 3-dimensional volume data are acquired by scanning the target object, the object (e.g., expectant mother or fetus) may be moved. This makes it difficult to accurately detect the heartbeat period of the fetus. Accordingly, the ultrasound system may further include a motion compensating unit. The motion compensating unit compensates for the motion of the expectant mother or the fetus by matching the brightness of pixels between a previously set VOI and a currently set VOI. The motion compensating unit may be operable to calculate the motion vectors by summing the absolute differences of brightness of pixels between the previously set VOI and the currently set VOI. For example, assuming that the VOI at a $n^{th}$ frame is expressed as V'''(m), the VOI at a next frame can be expressed as V'''(m+1). In such a case, a variable m represents the combination of n−1, n and n+1. The motion compensating unit may move V'''(m) up, down, right and left (i, j), and then calculate the absolute differences of brightness of pixels between V'''(m) and V'''(m+1) at each position. A motion vector may be estimated at a position where the absolute difference is minimal. The sum of the absolute difference is calculated as the following equation.

$$SAD_n(i,j) = \sum_{m=-1}^{1} \sum_{l=0}^{M-1} \sum_{k=n_T}^{n_B} |V^n(m,k,l) - V_{i,j}^n(m+1,k,l)| \quad (8)$$

$$\text{for } -W \le i, j < W, 1 \le n < K-1$$

wherein, W represents a predefined motion estimated range, K represents a total number of the frames, i, j represent motion displacements, k,l represent the position of a pixel in the frame included in VOI, and m represents the number of the frames.

The input unit 140 may receive setup information from a user. The setup information may include reference frame setup information, M-mode line setup information and rotation setup information of a 3-dimensional ultrasound image. The processor 150 may be operable to form an M-mode image signal. The M-mode image may be formed by using the reconstructed volume data based on the setup information inputted from a user through the input unit 140.

Figure 14:
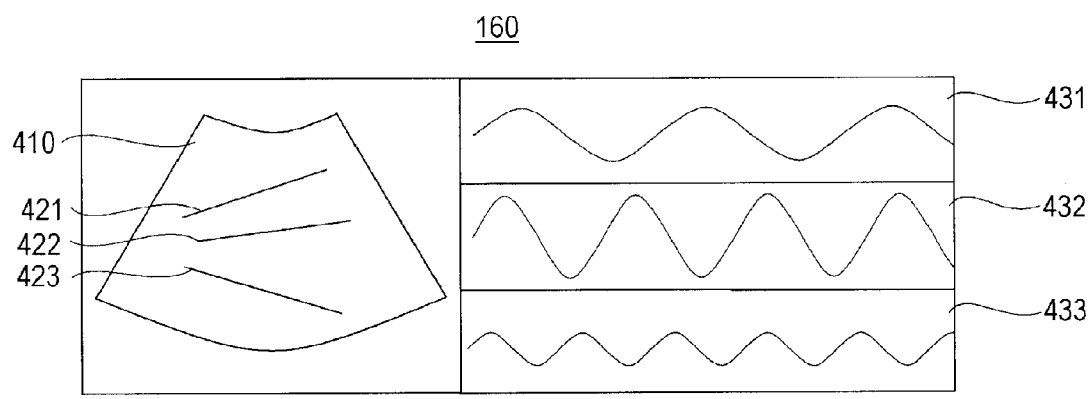
FIG. 14 is a schematic diagram showing a reference frame image and M-mode images in accordance with one embodiment of the present invention.

The processor 150 may form a reference frame image 410 by using the reconstructed volume data based on the reference frame setup information as illustrated in FIG. 14. Then, the processor 150 may extract data corresponding to M-mode lines 421, 422 and 423, which are set on the reference frame, based on the M-mode line setup information inputted through the input unit 140. The processor 150 may form M-mode images 431, 432 and 433 corresponding to the M-mode lines based on the extracted data. Although it is described that three M-mode lines are set on the reference frame image for ease of explanation in accordance with one embodiment of the present invention, the M-mode lines may be arbitrarily set on the reference frame image in accordance with another embodiment.

Further, a different reference frame image may be formed based on reference frame setup information while the previously formed M-mode images 431, 432 and 433 are displayed. In such a case, at least one M-mode line may be set on each of the different reference frame images. Also, at least one M-mode image corresponding to the M-mode line may be formed by extracting data from the reconstructed volume data.

In accordance with another embodiment of the present invention, reference frame setup information for forming a plurality of reference frame images may be inputted through the input unit 140. The processor 150 may form reference frame images by using the reconstructed volume data based on the reference frame setup information. At least one M-mode line may be set on each reference frame image. The processor 150 may extract data corresponding to the M-mode line set on each reference frame image from the reconstructed volume data and forms M-mode image signals for M-mode images based on the extracted data.

Figure 15:
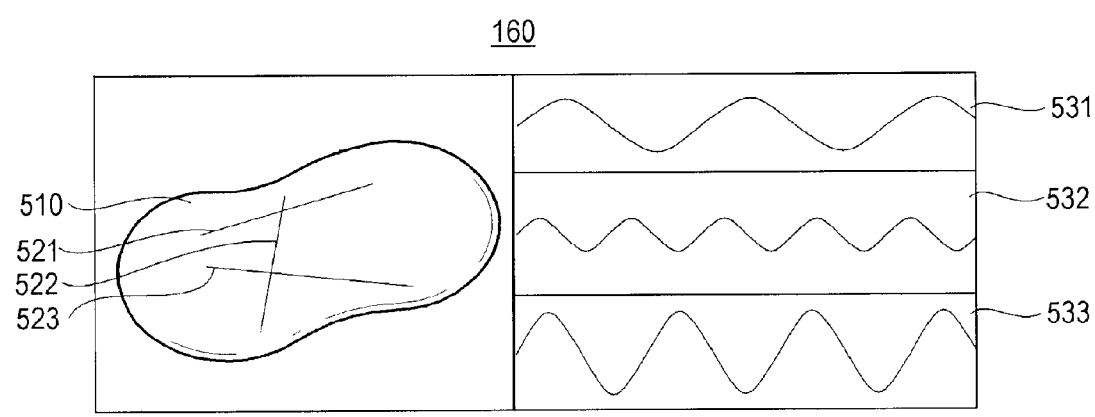
FIG. 15 is a schematic diagram showing a 3-dimensional ultrasound image and M-mode images in accordance with another embodiment of the present invention.

In accordance with yet another embodiment of the present invention, the processor 150 may form a 3-dimensional ultrasound image 510 as illustrated in FIG. 15 by using the reconstructed volume data. M-mode lines 521, 522 and 523 may be set on the 3-dimensional ultrasound image 510 based on M-mode line setup information inputted from the user through the input unit 140. The processor 150 may extract data corresponding to the M-mode lines 521, 522 and 523 set on the 3-dimensional ultrasound image and form M-mode images based on the extracted data. Although the three M-mode lines are set, the number of the M-mode lines is not limited thereto. If the rotation setup information is inputted through the input unit 140, then the processor 150 may be operable to rotate the 3-dimensional ultrasound image.

Thereafter, M-mode lines may be set on the rotated 3-dimensional ultrasound image and the processor 150 may form M-mode images corresponding to the M-mode lines set on the rotated 3-dimensional ultrasound image.

The display unit 160 may receive the reference frame image signals, the 3-dimensional ultrasound image signals and the M-mode image signals to display the reference frame image, the 3-dimensional ultrasound image and the M-mode image.

As mentioned above, the present invention may display M-mode images for different portions of the target object without moving a probe.

In accordance with one embodiment of the present invention, there is provided an ultrasound system, including: a probe operable to transmit ultrasound signals to a target object containing a periodically moving object and receive ultrasound echo signals reflected from the target object; a volume data forming and reconstructing unit operable to form volume data based on the ultrasound echo signals, the volume data forming and reconstructing unit being configured to determine a beat period of the moving object and reconstruct the volume data based on the beat period; a processor operable to form at least one reference image based on the reconstructed volume data and set a plurality of M-mode lines on the reference image, the processor being configured to form a plurality of M-mode images by extracting data corresponding to the M-mode lines from the reconstructed volume data; and a display unit to display the reference image, the M-mode lines and the M-mode images, one at a time, simultaneously or sequentially.

In accordance with another embodiment of the present invention, there is provided a method of forming an ultrasound image, including: a) transmitting ultrasound signals to a target object containing a periodically moving object and receiving ultrasound echo signals reflected from the target object; b) forming volume data based on the ultrasound echo signals; c) determining a beat period of the moving object and reconstructing the volume data based on the beat period; d) forming at least one reference image based on the reconstructed volume data; e) setting a plurality of M-mode lines on the reference image; f) forming a plurality of M-mode images by extracting data corresponding to the plurality of M-mode lines from the reconstructed volume data; and g) displaying the reference image, the M-mode lines and the M-mode images, one at a time, simultaneously or sequentially.

Any reference in this specification to "one embodiment," "an embodiment," "example embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system comprising:
a probe configured to transmit ultrasound signals to a target object containing a periodically moving object and to receive ultrasound echo signals reflected from the target object;
a processor configured to generate volume data based on the ultrasound echo signals;
a display configured to display a 3-dimensional ultrasound image constructed based on the volume data; and
a user input configured to receive user inputs regarding reference image setup information and M-mode line setup information associated with the 3-dimensional ultrasound image,
wherein the processor is further configured to generate a reference image representing a plane cut through the 3-dimensional ultrasound image using the volume data, the cut plane designated based on the reference image setup information and to generate an M-mode line on the reference image which is designated based on the M-mode line setup information, and
M-mode images are generated and displayed based on the M-mode line on the reference image which is designated using the 3-dimensional ultrasound image.

2. The ultrasound system of claim 1, wherein the user input is further configured to receive rotation information upon the 3-dimensional ultrasound image, and
the processor is further configured to control a rotation of the 3-dimensional ultrasound image displayed on the display based on the rotation information so that the reference image and the M-mode line can be designated by a user using the 3-dimensional ultrasound image rotated to any one of a plurality of viewing angles.

3. The ultrasound system of claim 2, wherein the processor is further configured to determine a moving period of the periodically moving object and interpolate the volume data to contain a same number of frames in each moving period.

4. A method comprising:
using a probe to transmit ultrasound signals to a target object containing a periodically moving object and receiving ultrasound echo signals reflected from the target object;
generating volume data based on the ultrasound echo signals;
displaying a 3-dimensional ultrasound image constructed based on the volume data;
receiving user inputs regarding reference image setup information and M-mode line setup information associated with the 3-dimensional ultrasound image;
generating a reference image representing a plane cut through the 3-dimensional ultrasound image using the volume data, the cut plane being designated based on the reference image setup information;
generating a M-mode line on the reference image which is designated based on the M-mode line setup information; and
displaying M-mode images based on the M-mode line on the reference image which is designated using the 3-dimensional ultrasound image.

5. The method of claim 4, further comprising:
receiving a user input regarding rotation information upon the displayed 3-dimensional ultrasound image; and
rotating the displayed 3-dimensional ultrasound image based on the rotation information so that the reference image and the M-mode line can be designated by a user using the 3-dimensional ultrasound image rotated to any one of a plurality of viewing angles.

6. The method of claim 5, further comprising:
determining a moving period of the periodically moving object; and
interpolating the volume data to contain a same number of frames in each moving period.

7. An ultrasound system comprising:
a probe configured to transmit ultrasound signals to a target object containing a periodically moving object and to receive ultrasound echo signals reflected from the target object;
a processor configured to generate volume data based on the ultrasound echo signals and a period of the moving object;
a display configured to display a 3-dimensional ultrasound image constructed based on the volume data; and
a user input configured to receive a user input as to M-mode line setup information associated with the 3-dimensional ultrasound image,
wherein the processor is further configured to generate a reference image representing a plane cut through the 3-dimensional ultrasound image using the volume data, and to generate an M-mode line on the reference image based on the M-mode line setup information, and
M-mode images corresponding to the M-Mode line on the reference image are generated and displayed.

8. A method comprising:
transmitting ultrasound signals, by a probe, to a target object containing a periodically moving object and receiving ultrasound echo signals reflected from the target object;
generating volume data based on the ultrasound echo signals and a period of the moving object;
displaying a 3-dimensional ultrasound image constructed based on the volume data;
receiving a user input as to M-mode line setup information associated with the 3-dimensional ultrasound image;
generating a reference image representing a plane cut through the 3-dimensional ultrasound image using the volume data;
generating a M-mode line on the reference image based on the M-mode line setup information; and
displaying M-mode images corresponding to the M-Mode line on the reference image.

* * * * *